(12) United States Patent
Justin et al.

(10) Patent No.: US 7,578,836 B2
(45) Date of Patent: *Aug. 25, 2009

(54) ORTHOPEDIC SCREW AND METHOD

(75) Inventors: Daniel F. Justin, Logan, UT (US);
Thomas Wade Fallin, Hyde Park, UT (US); Thomas F. Winters, Winter Park, FL (US)

(73) Assignee: Depuy Mitek, Raynham, MA (US)

( * ) Notice: Subject to any disclaimer, the term of this patent is extended or adjusted under 35 U.S.C. 154(b) by 510 days.

This patent is subject to a terminal disclaimer.

(21) Appl. No.: 11/338,259

(22) Filed: Jan. 24, 2006

(65) Prior Publication Data
US 2006/0122612 A1 Jun. 8, 2006

Related U.S. Application Data

(60) Division of application No. 10/206,073, filed on Jul. 25, 2002, now Pat. No. 6,989,014, which is a continuation of application No. 09/542,100, filed on Apr. 4, 2000, now Pat. No. 6,468,277.

(51) Int. Cl.
*A61F 2/08* (2006.01)
(52) U.S. Cl. .................. 606/916; 606/304; 606/305; 606/317
(58) Field of Classification Search ............. 606/72, 606/73, 75, 76, 77, 65, 916, 316, 86 B, 87, 606/304, 305, 317; 81/460, 451, 436; 411/403, 411/404, 358, 364, 400; 433/174, 175, 176
See application file for complete search history.

(56) References Cited

U.S. PATENT DOCUMENTS

| 65,651 | A | 6/1867 | Davies |
| 146,023 | A | 12/1873 | Russell |
| 197,467 | A | 11/1877 | Harvey |
| 197,933 | A | 12/1877 | Harvey |

(Continued)

FOREIGN PATENT DOCUMENTS

CA 731381 4/1966

(Continued)

OTHER PUBLICATIONS

Herbert, "Bone Screws for Small Bone Fractures," *Zimmer*, 97-1152-01, 1992, pp. 1-14.

*Primary Examiner*—Pedro Philogene
(74) *Attorney, Agent, or Firm*—Allen Dyer Doppelt Milbrath & Gilchrist

(57) ABSTRACT

A screw, driving device, and method are provided for repairing a tissue injury of a patient, such as a meniscal tear in a knee or osteochondritis dissecans. The screw has a root, a distal section having a narrowing cross section toward the distal end, and a thread along at least a portion of the root between the proximal end and the distal end. Along a leading section extending from the distal end, the helical pitch is substantially constant; along a trailing section between the leading section and the root's proximal end, the helical pitch decreases. The substantially constant pitch along the leading section assists in preventing a stripping of the helical section. At the proximal end is a head having a diameter greater than a major root diameter of the central section. The head is for improving the tissue retention characteristics of the screw.

8 Claims, 4 Drawing Sheets

U.S. PATENT DOCUMENTS

| | | |
|---|---|---|
| 1,980,093 A | 11/1934 | Rosenberg |
| 2,165,149 A | 7/1939 | Olson |
| 2,263,137 A | 11/1941 | Oestreicher |
| 2,356,098 A | 8/1944 | Steinle et al. |
| 2,377,405 A | 6/1945 | Davies |
| 2,382,019 A | 8/1945 | Miller |
| 2,383,231 A | 8/1945 | Anderton |
| 2,419,555 A | 4/1947 | Fator |
| 2,633,091 A | 3/1953 | Wenger et al. |
| 2,801,631 A | 8/1957 | Charnley |
| 2,842,180 A | 7/1958 | Brown et al. |
| 3,051,169 A | 8/1962 | Grath |
| 3,079,181 A | 2/1963 | Van Der Wissel |
| 3,124,408 A | 3/1964 | Oestereicher |
| 3,233,500 A | 2/1966 | De Vellier |
| 3,454,070 A | 7/1969 | Phipard, Jr. |
| 3,664,540 A | 5/1972 | Witkin |
| 3,799,229 A | 3/1974 | Johnson |
| 3,861,269 A | 1/1975 | Laverty |
| 3,915,162 A | 10/1975 | Miller |
| 4,027,573 A | 6/1977 | Laverty |
| 4,058,856 A | 11/1977 | Doerre et al. |
| 4,059,102 A | 11/1977 | Devas |
| 4,069,980 A | 1/1978 | Yarem et al. |
| 4,175,555 A | 11/1979 | Herbert |
| 4,340,184 A | 7/1982 | Poss |
| 4,456,005 A | 6/1984 | Lichty |
| 4,463,753 A | 8/1984 | Gustilo |
| 4,468,200 A | 8/1984 | Münch |
| 4,537,185 A | 8/1985 | Stednitz |
| 4,640,271 A | 2/1987 | Lower |
| 4,723,541 A | 2/1988 | Reese |
| 4,842,464 A | 6/1989 | Green |
| 4,844,676 A | 7/1989 | Adamek |
| 4,854,311 A | 8/1989 | Steffee |
| 4,863,383 A | 9/1989 | Grafelmann |
| 4,873,976 A | 10/1989 | Schreiber |
| 4,884,572 A | 12/1989 | Bays et al. |
| 4,892,429 A | 1/1990 | Giannuzzi |
| 4,895,148 A | 1/1990 | Bays et al. |
| 4,917,554 A | 4/1990 | Bronn |
| 4,940,467 A | 7/1990 | Tronzo |
| 4,950,270 A | 8/1990 | Bowman et al. |
| 4,959,064 A | 9/1990 | Engelhardt |
| 5,019,078 A | 5/1991 | Perren et al. |
| 5,019,079 A | 5/1991 | Ross |
| 5,042,982 A | 8/1991 | Harms et al. |
| 5,059,206 A | 10/1991 | Winters |
| 5,085,660 A | 2/1992 | Lin |
| 5,120,171 A | 6/1992 | Lasner |
| 5,147,363 A | 9/1992 | Härle |
| 5,152,790 A | 10/1992 | Rosenberg et al. |
| 5,169,400 A | 12/1992 | Mühling et al. |
| 5,180,382 A | 1/1993 | Frigg et al. |
| 5,190,426 A | 3/1993 | Wieder et al. |
| 5,226,766 A | 7/1993 | Lasner |
| 5,246,441 A | 9/1993 | Ross et al. |
| 5,252,016 A | 10/1993 | Schmid et al. |
| 5,259,398 A | 11/1993 | Vrespa |
| 5,300,076 A | 4/1994 | Leriche |
| 5,306,275 A | 4/1994 | Bryan |
| RE34,871 E | 3/1995 | McGuire et al. |
| D356,868 S | 3/1995 | Broberg et al. |
| 5,403,136 A | 4/1995 | Mathys |
| 5,470,334 A * | 11/1995 | Ross et al. ............... 606/72 |
| 5,484,440 A | 1/1996 | Allard |
| 5,492,442 A | 2/1996 | Lasner |
| 5,536,127 A | 7/1996 | Pennig |
| 5,562,672 A | 10/1996 | Huebner et al. |
| 5,562,704 A | 10/1996 | Tamminmäki et al. |
| 5,569,252 A | 10/1996 | Justin et al. |
| 5,569,264 A | 10/1996 | Tamminmäki et al. |
| 5,571,139 A | 11/1996 | Jenkins, Jr. |
| 5,730,744 A | 3/1998 | Justin et al. |
| 5,743,912 A | 4/1998 | Lahille et al. |
| 5,779,704 A | 7/1998 | Kim |
| 5,871,486 A | 2/1999 | Huebner et al. |
| 5,964,768 A * | 10/1999 | Huebner ............... 606/73 |
| 6,030,162 A | 2/2000 | Huebner |
| 6,045,554 A * | 4/2000 | Grooms et al. ............... 606/73 |
| 6,468,277 B1 * | 10/2002 | Justin et al. ............... 606/65 |
| 6,506,192 B1 | 1/2003 | Gertzman et al. |
| 6,527,777 B2 * | 3/2003 | Justin ............... 606/73 |

FOREIGN PATENT DOCUMENTS

| | | |
|---|---|---|
| CA | 1007493 | 3/1977 |
| DE | 2618344 | 8/1977 |
| DE | 3215228 | 11/1983 |
| DE | 3630863 A1 | 3/1988 |
| DE | 4021550 | 1/1991 |
| EP | 0172130 | 2/1986 |
| EP | 0544868 B1 | 8/1995 |
| FR | 2588332 | 4/1987 |
| GB | 598834 | 2/1948 |
| IT | 365613 | 12/1938 |
| JP | 45-24729 | 8/1964 |
| SU | 77837 | 6/1918 |
| SU | 1216-466 A | 3/1986 |
| WO | WO 89/09030 | 10/1989 |
| WO | WO 90/02526 | 3/1990 |
| WO | WO 91/09572 | 7/1991 |
| WO | WO 93/00518 | 1/1993 |
| WO | WO 94/16636 | 8/1994 |
| WO | WO 95/15727 | 6/1995 |

* cited by examiner

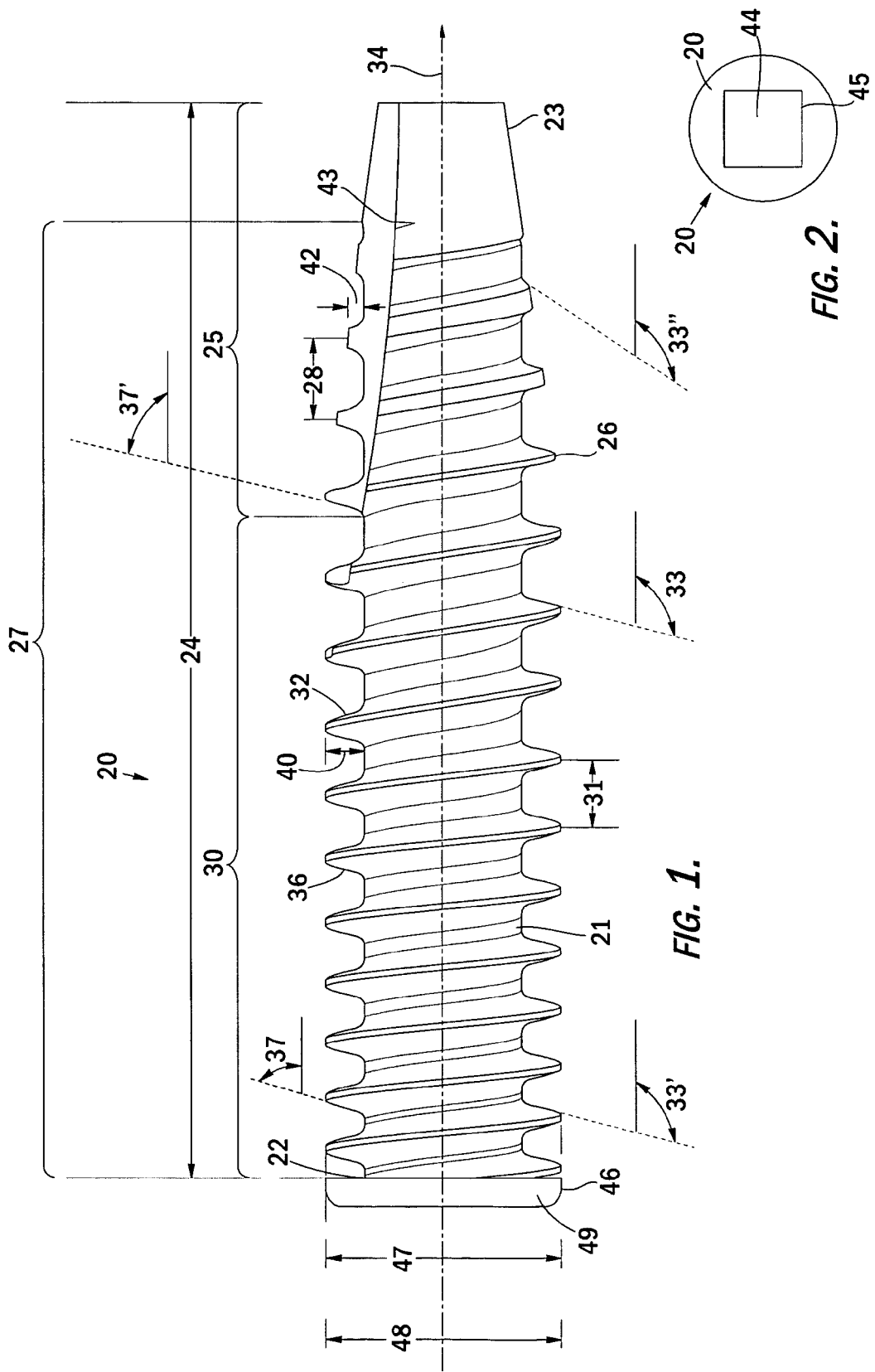

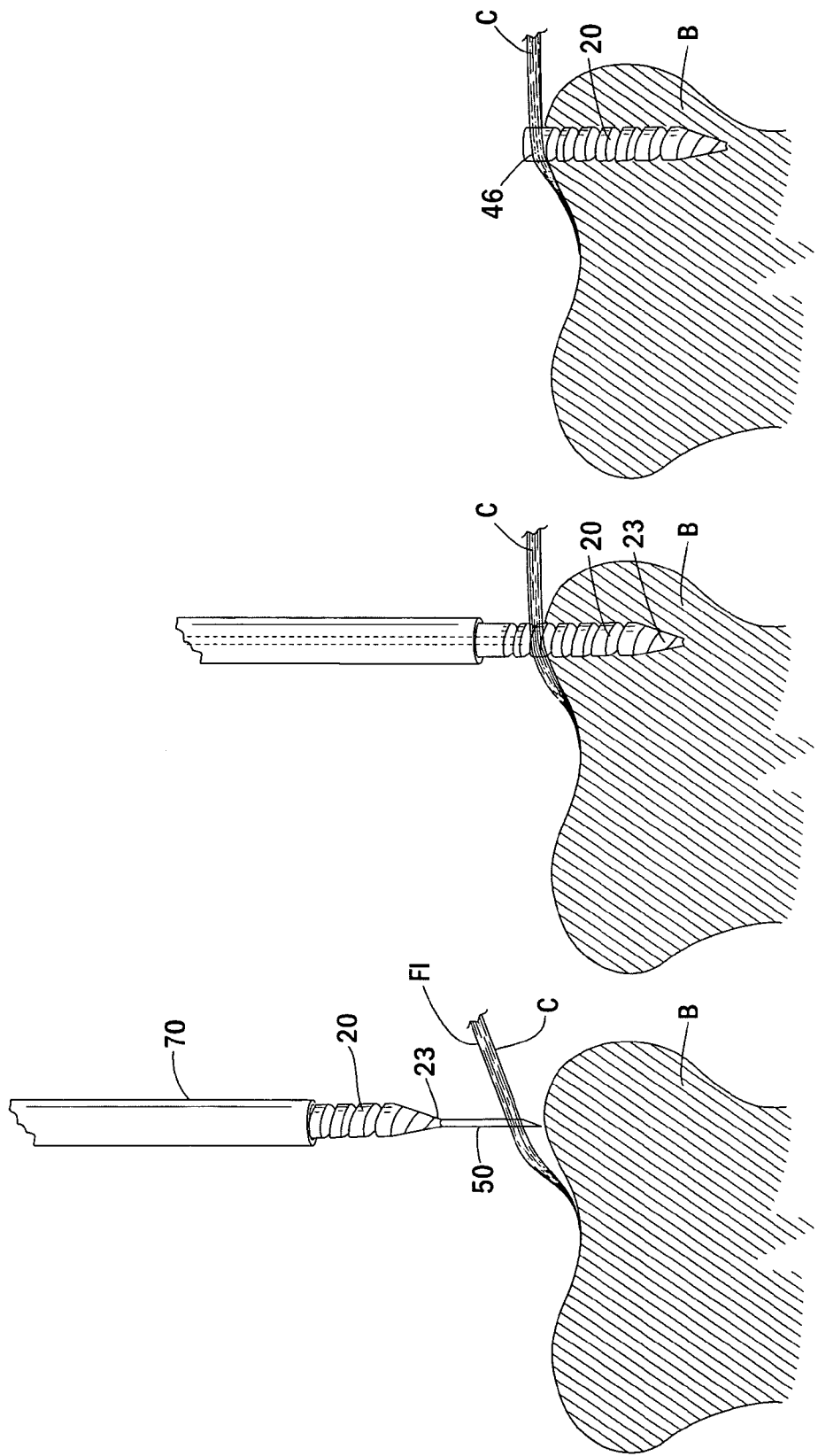

ORTHOPEDIC SCREW AND METHOD

CROSS-REFERENCE TO RELATED APPLICATIONS

This application is a divisional of and incorporates by reference application Ser. No. 10/206,073, filed Jul. 25, 2002, now issued U.S. Pat. No. 6,989,014, which was a continuation of application Ser. No. 09/542,100, filed Apr. 4, 2000, now issued U.S. Pat. No. 6,468,277, both of which are commonly owned with the present invention and which are incorporated herein by reference.

BACKGROUND OF THE INVENTION

1. Field of the Invention

The present invention relates to surgical devices and methods for repairing orthopedic injuries, and, more particularly, to devices and methods for repairing soft-tissue tears and for affixing soft tissue to bone.

2. Description of Related Art

The repair of soft tissue tears represents a persistent problem in orthopedic practice. It is known to apply sutures and various types of fixation devices to such tears. The fixation of soft tissue to a bone, and that of bone pieces to each other, is an additional frequently encountered problem. A related condition, osteochondritis dissecans (OCD), results in the splitting of pieces of cartilage into a joint, such as a knee joint or shoulder joint.

Sutures, barbs, and various types of screws are known to be used to bring two sides of a tear into apposition; screws are also known for use in fixing two sections of bone together and for fixing a piece of soft tissue to bone. A number of fastener-type devices are known in the art: Screiber (U.S. Pat. No. 4,873,976); Bays et al. (U.S. Pat. Nos. 4,884,572 and 4,895,148); Winters (U.S. Pat. No. 5,059,206); and Justin and Winters (U.S. Pat. Nos. 5,503,634 and 5,730,744). Bone screws are disclosed by Huebner et al. (U.S. Pat. Nos. 5,562,672, 5,871,486, and 5,964,768).

SUMMARY OF THE INVENTION

It is an object of the present invention to provide a screw, delivery device, and method for repairing an orthopedic injury.

It is a further object to provide such a screw that is made from a nontoxic, biocompatible, bioabsorbable plastic specially designed to maintain its structural integrity during the healing of the tear and to prevent tissue abrasion.

It is an additional object to provide such a screw having a shape designed to compress a tear and to pull soft tissue onto a bone.

It is another object to provide such a screw shaped to resist forces tending to pull apart a tear during healing or to pull soft tissue away from a bone.

It is also an object to provide such a screw that resists stripping and has superior tissue retention characteristics.

These and other objects are attained with the screw and delivery device system and method of the present invention, an orthopedic screw for repairing a tear in soft tissue of a patient, for affixing soft tissue to a bone, and for affixing a condyle to a bone surface. The fastener has a head at a proximal end and a root extending between the head and a distal end. A distal section of the root has a narrowing cross section toward the distal end. In use an insertion of the fastener into soft tissue is facilitated by this narrowed distal end, which takes the form in a preferred embodiment of a generally conical-shaped distal tip as a lead-in geometry of the root.

The fastener further has a helical thread, a protrusion that extends along at least a portion of the root. A leading end of the thread begins at a location in spaced relation from the distal end, and a trailing end of the thread meets the head at the root's proximal end. Along a leading section the thread extends from the leading end and has a substantially constant helical pitch; along a trailing section between the distal section and the trailing end, the thread has a helical pitch that decreases in a proximal direction, so that the pitch adjacent the head is smaller than that along the distal section. In use the decrease in the helical pitch along the trailing section serves to bring two pieces of tissue into apposition as the screw is advanced across the two pieces of tissue in a screwing motion. The substantially constant pitch along the leading section assists in preventing a stripping of the thread, which is more likely to occur with a screw having a variable pitch along a leading section.

At the proximal end the head has a diameter greater than a major root diameter of the proximal section. The head is for improving the tissue retention characteristics of the screw.

In an alternate embodiment, the thread also has means for resisting an axial force from pulling the screw out of the tissue and from pulling the two pieces of tissue apart. Specifically, the resisting means comprises the thread having a buttress form.

In a preferred embodiment, the screw material comprises a biodegradable plastic biocompatible with the soft tissue of the patient. The material is specifically designed to be biodegradable within a first time span greater than or equal to a second time span over which the two pieces of tissue can knit together. This feature permits the fastener to remain in place for as long as required for the tissue to heal, but ultimately to biodegrade and be dissipated harmlessly into the patient's system. Alternatively, the material in some procedures may be desired to be nonbiodegradable and remain in place permanently or until surgical removal.

The material is further preferably designed to have elastomeric properties compliant with those of the tissue to be repaired in order to confer biofunctionality.

A further feature of the present invention comprises a delivery device for introducing the above-described screw into the area of the patient's tissue to be repaired. A feature of the screw permitting a mating with a delivery device comprises the screw's having an axial bore extending along the helical axis proceeding from the proximal end. The bore preferably has a noncircular cross-sectional shape so that an elongated driving device having a noncircular cross-sectional shape and dimensioned to pass into the bore can enter the bore and turn the screw. The screw can then be advanced into the target tissue by being rotated by the driving device in a direction having a handedness commensurate with the thread. Simply put, the screw is internally drivable by rotation of an elongated member inserted into its bore, which then also supports the screw by imparting additional rigidity during the driving procedure. This is a desired feature if the screw material is flexible.

The elongated driving device of the present invention for driving the screw as described above has a distal end having means for mating with the screw's proximal end, and a proximal end having means for being rotationally driven. In use the screw is mated with the driving device's distal end, the screw and distal end of the driving device are positioned adjacent the first piece of tissue, and the means for being driven is rotated in a direction having a handedness commensurate with the thread, thereby advancing the screw into the tissue pieces until the separation therebetween is breached.

In a specific embodiment of the system, the driving device further has a noncircular cross-sectional shape along a distal section adjacent the distal end. The screw's bore as described above has a noncircular cross-sectional shape dimensioned to permit the distal section of the driving device to pass into the bore and to permit relative axial sliding and rotational coupling movement therebetween. The axial slidability permits the driving device to be mated by sliding the driving device distal section into the fastener bore and to be removed once the tissue pieces have been joined together by sliding the driving device out of the bore.

The method of the present invention is for repairing an orthopedic tissue injury in a patient. The method comprises the steps of providing a screw having the features as described above. The screw is then inserted into an area adjacent the first piece of tissue. The distal end of the screw is manipulated to a desired position. In the case of a tear, the desired position is generally normal to a long axis of the tear, and the screw is driven across the tear in a screwing motion. The decrease in the helical pitch serves to bring two sides of the tear into apposition as the screw is advanced. In the case of attaching and/or drawing two pieces of tissue together, the desired position is through one piece of tissue and adjacent the second piece. The screw is driven through the first piece of tissue and into the second, with the decrease in helical pitch bringing the two pieces of tissue together.

The features that characterize the invention, both as to organization and method of operation, together with further objects and advantages thereof, will be better understood from the following description used in conjunction with the accompanying drawing. It is to be expressly understood that the drawing is for the purpose of illustration and description and is not intended as a definition of the limits of the invention. These and other objects attained, and advantages offered, by the present invention will become more fully apparent as the description that now follows is read in conjunction with the accompanying drawing.

BRIEF DESCRIPTION OF THE DRAWINGS

FIG. 1 is a side perspective view of the orthopedic screw of the present invention.

FIG. 2 shows the screw in cross section.

FIG. 4A-4C illustrate a method for repairing osteochondritis dissecans.

DETAILED DESCRIPTION OF THE PREFERRED EMBODIMENTS

Figure 3A:
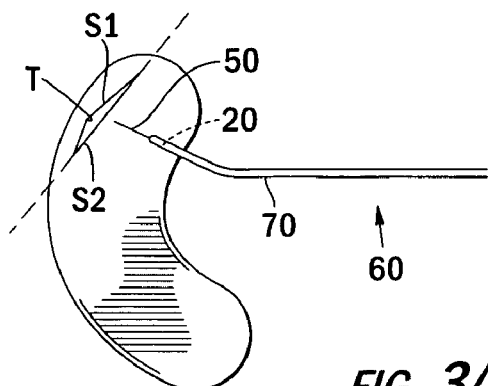
FIGS. 3A-3D illustrate a method for repairing a knee meniscal tear.

A description of the preferred embodiments of the present invention will now be presented with reference to FIGS. 1-4C.

The preferred exemplary embodiment of the present invention comprises a system 10 comprising a screw 20 and an elongated driving device 60, and a method for repairing a soft-tissue tear in a patient.

In a preferred embodiment shown in FIGS. 1 and 2, the screw 20 has a root 21 that has a proximal end 22, a distal end 23, and a length 24. The root 21 further has a distal section 25 tapering toward the distal end 23, in this specific embodiment the distal section 25 generally forming a cone as a lead-in geometry. Alternatively, a self-tapping distal section could be implemented. In use an insertion of screw 20 into the target tissue is facilitated by the conical-shaped distal section 25. The proximal section 30 of the root 21 has a substantially constant radius.

A helical protrusion (i.e., a thread) 26 proceeds atop the root 21 between the proximal end 22 and the distal end 23. A short section adjacent the distal end 23 is substantially smooth and is not threaded. The thread 26 has a helical pitch that has a substantially constant value 28 along a leading section 27 extending proximal of the distal end 23. Extending proximal of the leading section 27, along a trailing section 30, the thread 26 has a variable value 31, decreasing in a proximal direction to the proximal end 22. In use the decrease in helical pitch along the trailing section 30 serves to bring two pieces S1,S2 of a tissue T into apposition as the screw 20 is advanced thereacross in a screwing motion.

Preferably the thread 26 has a buttress form for resisting an axial force from pulling the screw out of the tissue and from pulling the two pieces of tissue apart. The "buttress form," is a term known in the art of tool making, and is known to have advantages in applications involving high stresses along the longitudinal (helical) axis in one direction. The "pressure flank," the face of the protrusion taking the thrust, is generally desired to be nearly perpendicular to the helical axis so that the radial component of the thrust is reduced to a minimum.

In screw 20 the thread 26 further has a leading face 32 facing the distal end 23. The leading face 32 makes a first angle 33 with a helical axis vector 34 having a directionality pointing from the proximal 22 to the distal end 23. The first angle 33 decreases from a first oblique angle 33" adjacent the distal end 23 to a second oblique angle 33' adjacent the proximal end 22. The second oblique angle 33' is therefore smaller than the first oblique angle 33". The leading face 32 adjacent the proximal end 22 serves to resist an axial force in the direction of the helical axis vector 34.

In screw 20 the thread 26 further has a trailing face 36 facing the proximal end 22. The trailing face 36 makes a second angle 37 with the helical axis vector 34. The second angle 37 decreases from a first acute angle 37' adjacent the distal end 23 to a second acute angle 37 adjacent the proximal end 22. The second acute angle 37 is therefore smaller than the first acute angle 37'. The trailing face 36 adjacent the distal end 23 serves to resist an axial force in a direction opposite the direction of the helical axis vector 34.

The thread 26 also has a radial depth measured from the surface of the root 21 to the crest of the thread 26. The thread depth 40 along the trailing section 30 has a substantially constant value. The thread depth 42 along the leading section 29 decreases from the value 40 along the trailing section 30 to a minimum value at the distal end 43 of the thread 26.

The screw material in the preferred embodiment comprises a biodegradable plastic biocompatible with the tissue of the patient. Exemplary materials include a nontoxic blend of polycaprolactone and polyglycolide, a blend of polylactide and polyglycolide, pure polydioxanone, poly(ethylene oxide):poly(butylene terephthalate), polyorthoester, polyhydroxybutyrate, or cross-linked collagen. The material is designed to be sufficiently flexible and strong to withstand natural knee movement during healing. The material is also designed to be biodegradable within a first time span greater than or equal to a second time span over which the pieces S1,S2 of the tissue T can knit together. In other words, the material is resorbed over a time span commensurate with the healing process, so that, once the tissue T is healed, the screw 20 can gradually degrade, leaving healed tissue with no foreign material embedded therein.

In the preferred embodiment, screw 20 further has an axial bore 44 therethrough generally along the helical axis 34. In an alternate embodiment, the bore 44 may not extend completely through to the distal end 23. In the embodiment illustrated herein, bore 44 proceeds from proximal end 22 to distal end 23, and has a noncircular cross-sectional shape to permit an elongated driving device having a noncircular cross-sectional shape to pass into bore 44 and to advance screw 20 into the tissue, here shown as a meniscus M, by being rotated in a direction having a handedness commensurate with the thread 26 (see FIG. 3C). The cross-sectional shape 45 of the bore, as shown in FIG. 2, is square, although this is not intended as a limitation, as other noncircular bores may be contemplated by one of skill in the art.

The screw 20 further has a head 46 extending from the root's proximal end 22, the bore 44 extending therethrough as well. The head 46 has a diameter 47 at least as great as a maximum diameter 48 of the thread 26 and a substantially smooth periphery 49.

The driving device of a preferred embodiment comprises an elongated driver 60 comprising a needle 50 inserted through an elongated tubular member 70.

Figure 3B:
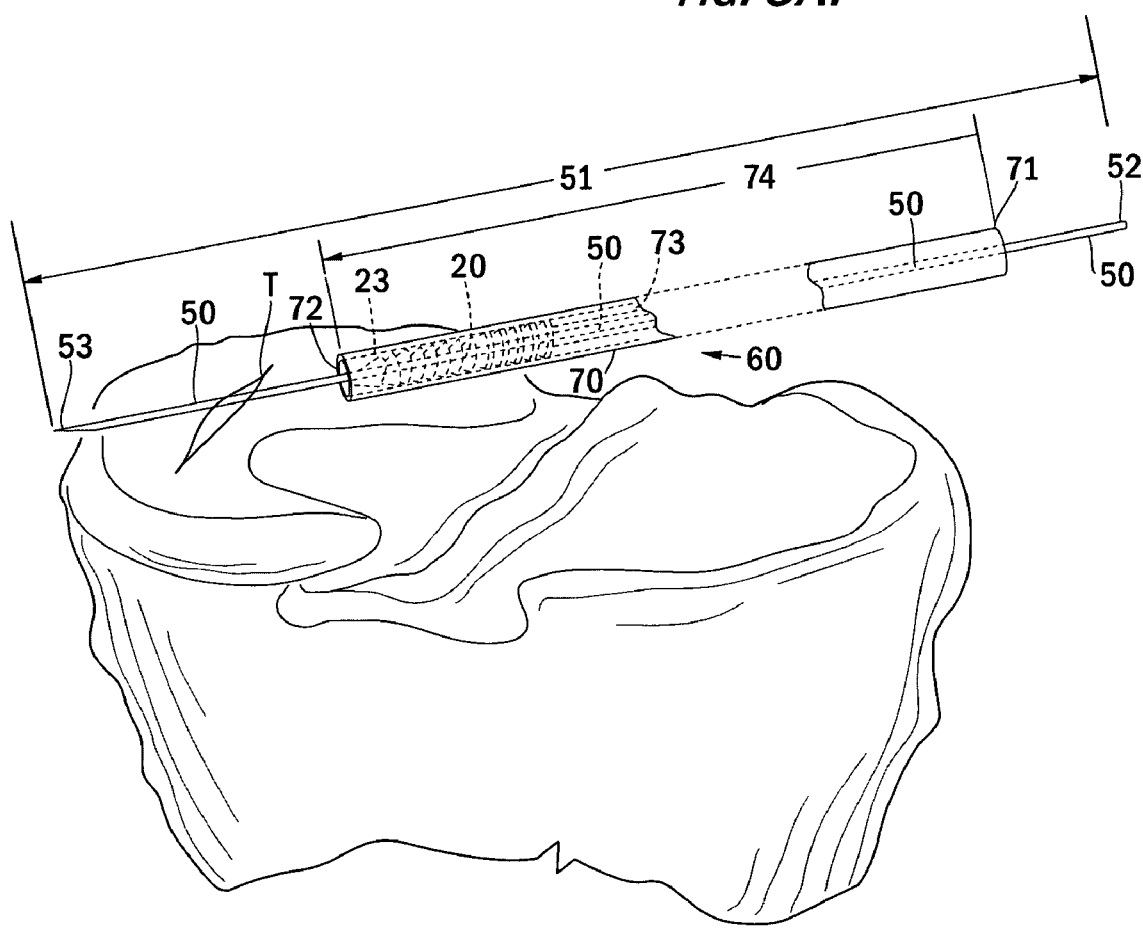
Figure 3C:
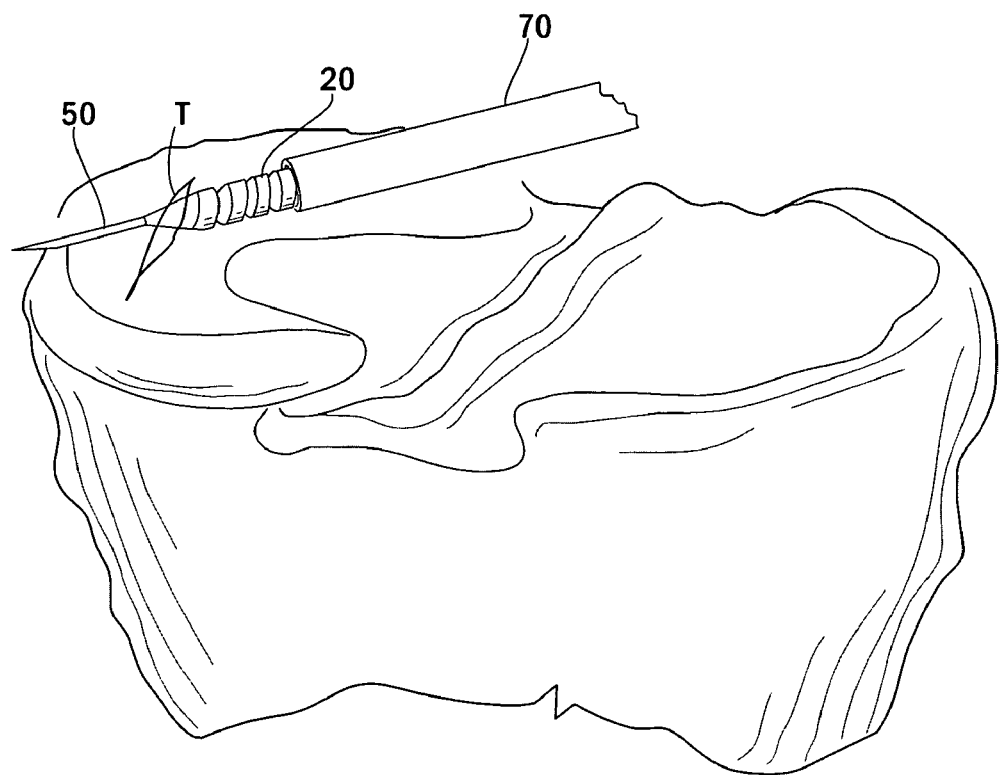

The needle 50 has a length 51, a proximal end 52, and a pointed distal tip 53 (see FIG. 3B). Needle 50 further has a square cross-sectional shape along at least a distal section dimensioned axially to be slidable through the bore 44 of the screw 20 and rotationally to drive the screw 20 (FIG. 3C).

In use needle 50 is axially movable distalward to a first position wherein the needle tip 53 protrudes from distal end 23 of screw 20 (FIG. 3A). In this position, needle tip 53 can pierce the tissue to be repaired (FIG. 3B), aiding in advancing the screw 20, preparatory to rotating the needle 50 and hence the screw 20, which are rotationally coupled.

A further component of system 10 comprises a cannula member 70 for protecting the screw 20 during insertion into the tissue area adjacent the tear T (see FIGS. 3A-3D). Cannula member 70 has a proximal end 71 and a distal end 72. In addition, cannula member 70 has an axial bore 73 therethrough from distal end 72 to proximal end 71. Bore 73 is dimensioned to permit the screw 20 and the needle 50 to fit therein and to permit sliding and rotational movement therebetween.

Cannula member 70 has a length 74 shorter than needle length 51, permitting distal tip 53 and proximal end 52 of needle 50 to protrude from distal end 72 and proximal end 71, respectively, of the cannula member 70.

In an embodiment for repairing osteochondritis dissecans, the method comprises the steps of moving the needle 50 axially into the screw's bore 44. Next the screw's distal end 23 is manipulated to a position adjacent a face F1 of a piece of cartilage C that has separated from an adjacent piece of bone B. The cartilage C is pierced with the needle tip 53, and the screw 20 is driven through the cartilage C and into the bone B in a screwing motion as above. The proximal decrease in the helical pitch serves to bring the cartilage C and the bone B into apposition as the screw 20 is advanced, until the screw head 46 is positioned atop the cartilage C, holding it in place.

In the embodiment contemplated for repairing a knee meniscus, the needle, the tubular member, and the cannula member all similarly have a curve therein for enabling an operator to manipulate the system into a position to approach a soft tissue tear around a curved radius. In the preferred embodiment, this curve comprises a 10-30 degree generally upward bend.

The method of the present invention for repairing a tear T in soft tissue of a patient, shown in FIGS. 3A-3D for repairing a meniscal tear, comprises the steps of moving the needle 42 axially through the bore 44 of the screw 20, the distal tip 53 of the needle 50 emerging from the distal end 23 of the screw 20 (FIG. 3A). The needle tip 53 then pierces the tear T, and the needle 50 is advanced across both sides S1,S2 (FIG. 3B).

The screw 20 is inserted over the needle 50 into an area of soft tissue adjacent the tear T. The operator then manipulates the distal end 23 of the screw 20 to a position generally normal to the long axis of the tear T (FIG. 3C).

Figure 3D:
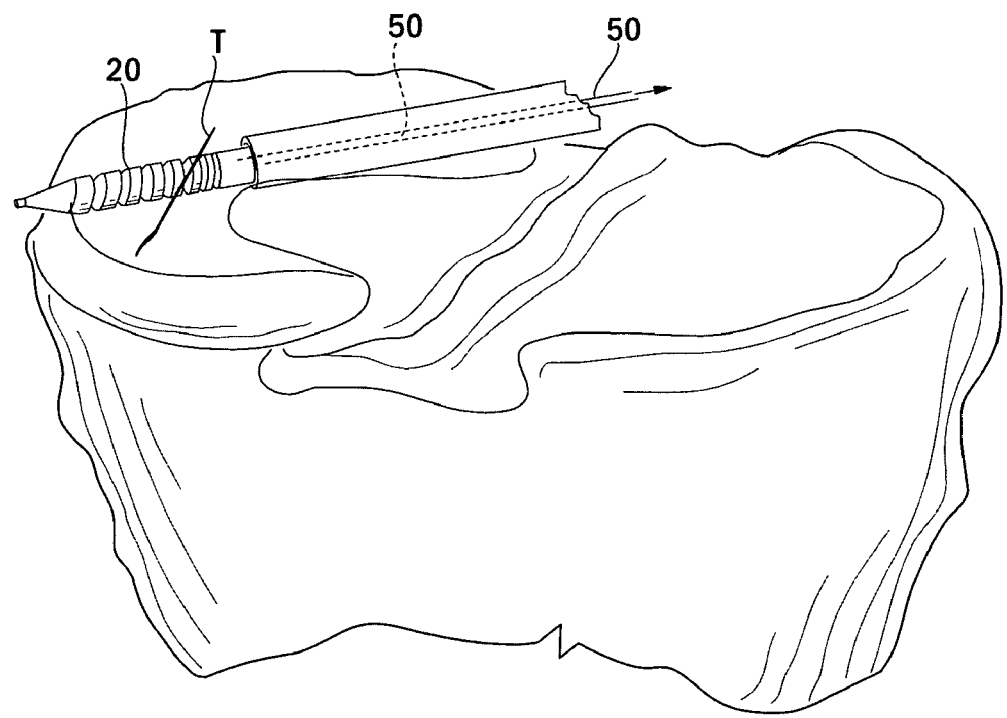

The next step comprises driving the screw 20 across the tear T in a screwing motion (FIG. 3C), the decrease in the helical pitch 31 serving to bring two sides of the tear S1,S2 into apposition as the screw 20 is advanced (FIG. 3D). Given the rotationally coupled needle 50 and screw 20, the driving step comprises rotating the needle 50 and hence the screw 20. Since the needle 50 and screw 20 are axially slidable relative to each other, the needle 50 can then be removed from the screw 20 and all instruments removed from the surgical site once the sides of the tear have been drawn together (FIG. 3D).

Another embodiment of the present invention comprises a method for repairing osteochondritis dissecans (OCD). In this method, illustrated in FIGS. 4A-4C, a needle 50 is moved axially into the screw bore, as above. The screw's distal end 23 is manipulated to a position adjacent a top face F1 of a piece of cartilage C that has separated from an adjacent piece of bone B (FIG. 4A).

The cartilage C is pierced with the needle tip 53, and the screw 20 is driven through the cartilage C and into the bone B in a screwing motion by rotating the needle 50 and hence the screw 20 (FIG. 4B). The proximal decrease in the helical pitch serves to bring the cartilage C and the bone B into apposition as the screw 20 is advanced, until the screw head 46 is positioned against the top face F1 the cartilage C (FIG. 4C).

It may be appreciated by one skilled in the art that additional embodiments may be contemplated, including fasteners, systems, and methods for repairing other soft tissue tears, such as in the shoulder.

In the foregoing description, certain terms have been used for brevity, clarity, and understanding, but no unnecessary limitations are to be implied therefrom beyond the requirements of the prior art, because such words are used for description purposes herein and are intended to be broadly construed. Moreover, the embodiments of the apparatus and method illustrated and described herein are by way of example, and the scope of the invention is not limited to the exact details of construction.

Having now described the invention, the construction, the operation and use of preferred embodiment thereof, and the advantageous new and useful results obtained thereby, the new and useful constructions, and reasonable mechanical equivalents thereof obvious to those skilled in the art, are set forth in the appended claims.

What is claimed is:

1. A system for repairing a tissue injury in a patient, the system comprising a screw having:
   a root having a proximal end and a distal section having a narrowing cross section toward a distal end;
   a thread atop the root along at least a portion thereof between the proximal end and the distal end, the thread having a helical pitch having a substantially constant value along a leading section extending proximal of the distal end and having a variable value along a trailing section extending proximal of the leading section, wherein the helical pitch decreases along the trailing section to the proximal end of the root, the thread further having a leading face facing the distal end, the leading face making a first angle with a helical axis having a directionality pointing from the proximal to the distal end, the first angle decreasing from a first oblique angle adjacent the distal end to a second oblique angle adjacent the proximal end, the second oblique angle smaller than the first oblique angle; and an axial bore at least partially therethrough generally along a helical axis proceeding from the proximal end and into the root, the bore having a noncircular cross-sectional shape; and an elongated driving device having:
a distal end having means for mating with the bore;
a proximal end having means for being rotationally driven; and
a noncircular cross-sectional shape along a distal section adjacent the distal end, the distal section dimensioned for entry into the bore and to permit relative axial sliding and rotational coupling movement therebetween.

2. The system recited in claim 1, wherein the screw further has a head extending from the root proximal end having a diameter at least as great as a maximum diameter of the thread, the head having a substantially smooth periphery, the bore extending through the head.

3. The system recited in claim 1, wherein the bore extends completely through the screw to the distal end, and the driving device comprises a needle having a pointed distal tip.

4. A system for repairing a tissue injury in a patient, the system comprising:
a screw having:
a root having a proximal end and a distal section having a narrowing cross section toward a distal end;
a thread atop the root along at least a portion thereof between the proximal end and the distal end, the thread having a helical pitch having a substantially constant value along a leading section extending proximal of the distal end and having a variable value along a trailing section extending proximal of the leading section, wherein the helical pitch decreases along the trailing section to the proximal end of the root, the thread further having a trailing face facing the proximal end, the trailing face making a second angle with the helical axis, the second angle decreasing from a first acute angle adjacent the distal end to a second acute angle adjacent the proximal end, the second acute angle smaller than the first acute angle; and
an axial bore at least partially therethrough generally along a helical axis proceeding from the proximal end and into the root, the bore having a noncircular cross-sectional shape; and an elongated driving device having:
a distal end having means for mating with the bore;
a proximal end having means for being rotationally driven; and
a noncircular cross-sectional shape along a distal section adjacent the distal end, the distal section dimensioned for entry into the bore and to permit relative axial sliding and rotational coupling movement therebetween.

5. The system recited in claim 4, wherein the screw further has a head extending from the root proximal end having a diameter at least as great as a maximum diameter of the thread, the head having a substantially smooth periphery, the bore extending through the head.

6. The system recited in claim 4, wherein the bore extends completely through the screw to the distal end, and the driving device comprises a needle having a pointed distal tip.

7. A method for affixing two pieces of tissue of a patient together, the method comprising the steps of:
moving a needle axially into a bore of a screw, the needle adapted to drive the screw, the screw having:
a root having a proximal end and a distal section having a narrowing cross section toward a distal end; and
a thread atop the root along at least a portion thereof between the proximal end and the distal end, the thread having a helical pitch having a substantially constant value along a leading section extending proximal of the distal end and having a variable value along a trailing section extending proximal of the leading section, wherein the helical pitch decreases along the trailing section to the proximal end of the root, the thread further having a leading face facing the distal end, the leading face making a first angle with a helical axis having a directionality pointing from the proximal to the distal end, the first angle decreasing from a first oblique angle adjacent the distal end to a second oblique angle adjacent the proximal end, the second oblique angle smaller than the first oblique angle;
manipulating the distal end of the screw to a position generally normal to a face of a first piece of tissue adjacent a separation between the first and a second piece of tissue;
piercing the first piece of tissue with a tip of the needle; and
driving the screw between the tissue pieces in a screwing motion by rotating the needle and hence the screw, the proximal decrease in the helical pitch serving to bring two pieces of tissue into apposition as the screw is advanced.

8. A method for affixing two pieces of tissue of a patient together, the method comprising the steps of:
moving a needle axially into a bore of a screw, the needle adapted to drive the screw, the screw having:
a root having a proximal end and a distal section having a narrowing cross section toward a distal end; and
a thread atop the root along at least a portion thereof between the proximal end and the distal end, the thread having a helical pitch having a substantially constant value along a leading section extending proximal of the distal end and having a variable value along a trailing section extending proximal of the leading section, wherein the helical pitch decreases along the trailing section to the proximal end of the root, the thread further having a trailing face facing the proximal end, the trailing face making a second angle with the helical axis, the second angle decreasing from a first acute angle adjacent the distal end to a second acute angle adjacent the proximal end, the second acute angle smaller than the first acute angle;
manipulating the distal end of the screw to a position generally normal to a face of a first piece of tissue adjacent a separation between the first and a second piece of tissue;
piercing the first piece of tissue with a tip of the needle; and
driving the screw between the tissue pieces in a screwing motion by rotating the needle and hence the screw, the proximal decrease in the helical pitch serving to bring two pieces of tissue into apposition as the screw is advanced.

\* \* \* \* \*

UNITED STATES PATENT AND TRADEMARK OFFICE
CERTIFICATE OF CORRECTION

PATENT NO. : 7,578,836 B2
APPLICATION NO. : 11/338259
DATED : August 25, 2009
INVENTOR(S) : Justin et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 611 days.

Signed and Sealed this

Seventh Day of September, 2010

David J. Kappos
*Director of the United States Patent and Trademark Office*